(12) United States Patent
Wang et al.

(10) Patent No.: US 12,133,857 B2
(45) Date of Patent: Nov. 5, 2024

(54) METHOD FOR PROLONGING HALF-LIFE OF THEANINE IN VIVO

(71) Applicant: Anhui Agricultural University, Hefei (CN)

(72) Inventors: Yijun Wang, Hefei (CN); Zhipeng Kan, Hefei (CN); Xiaochun Wan, Hefei (CN); Jinbao Huang, Hefei (CN); Kangyi Zhang, Hefei (CN); Yunqiu Yang, Hefei (CN); Xiaoyu Tang, Hefei (CN)

(73) Assignee: Anhui Agricultural University, Hefei (CN)

( * ) Notice: Subject to any disclaimer, the term of this patent is extended or adjusted under 35 U.S.C. 154(b) by 0 days.

(21) Appl. No.: 18/676,985

(22) Filed: May 29, 2024

(65) Prior Publication Data

US 2024/0316081 A1 Sep. 26, 2024

Related U.S. Application Data

(63) Continuation of application No. PCT/CN2023/100155, filed on Jun. 14, 2023.

(30) Foreign Application Priority Data

Jun. 8, 2023 (CN) .......................... 2023106851162

(51) Int. Cl.
*A61K 31/70* (2006.01)

(52) U.S. Cl.
CPC ..................... *A61K 31/70* (2013.01)

(58) Field of Classification Search
CPC ............................... A61K 31/70; C07H 15/12
See application file for complete search history.

(56) References Cited

U.S. PATENT DOCUMENTS

2013/0137653 A1* 5/2013 Yoo .................. A61P 17/10
536/29.1
2014/0357593 A1 12/2014 Lee et al.

FOREIGN PATENT DOCUMENTS

| CN | 105837487 A | 8/2016 |
| CN | 114786499 A | 7/2022 |
| JP | 2011195482 A | 10/2011 |

OTHER PUBLICATIONS

Anan, T., Japan Agricultural Research Quarterly, 1988, 22(3), p. 195-199. (Year: 1988).*
Liang et al., Tropical Journal of Pharmaceutical Research, 2015, 14(10), p. 1943-1949. (Year: 2015).*
Anan, Toyomasa et. al. "Changes in chemical components during the development of tea shoots and manufacture of green tea" Yasai, Chagyo Shikenjo Kenkyu Hokoku, B: Chagyo, vol. 4, pp. 25-91, Dec. 31, 1991.

* cited by examiner

*Primary Examiner* — Jonathan S Lau
(74) *Attorney, Agent, or Firm* — IPRO, PLLC; Na Xu

(57) ABSTRACT

The present disclosure discloses a method for prolonging half-life of theanine in vivo. According to the present disclosure, a specific theanine glycoside compound formed by modification with a specific monosaccharide is used for prolonging the half-life of the theanine in vivo, which can be used for preparing sustained release drugs, prolonging action time of drugs, reducing administration frequency and improving compliance of patients. With the method of the present disclosure, the theanine glycoside compound obtained after modification can have a broad application prospect and a high commercial value in scientific research and clinical application.

11 Claims, 6 Drawing Sheets

METHOD FOR PROLONGING HALF-LIFE OF THEANINE IN VIVO

TECHNICAL FIELD

The present disclosure belongs to the technical field of biomedicine, and in particular to a method for prolonging half-life of theanine in vivo.

BACKGROUND

Theanine is an important non-protein amino acid in tea leaves, which accounts for about 0.5%-2% of a dry weight of the tea leaves. The theanine has a short half-life in vivo. Generally, the blood drug concentration reaches a peak at about 0.5 h-1 h after oral administration, then is decreased, and is decreased to an initial concentration value after 8 h-12 h. In recent years, relevant studies have found that the theanine has many beneficial effects of resisting inflammation, relieving oxidative damage, promoting sedation and resisting depression (with reference to existing public literature: Untargeted and targeted mass spectrometry reveal the effects of theanine on the central and peripheral metabolomics of chronic unpredictable mild stress-induced depression in juvenile rats. *Journal of Pharmaceutical Analysis.* 2023, 13. 73-87), improving learning and memory abilities (with reference to existing public literature: Effect of theanine on learning and memory abilities of mice. Lin Xueling. *Food Science,* 2004, 25, 218-219), promoting sleep (with reference to existing public literature: Sleep-promoting effect of theanine on mice, *Food Science,* 2009, 30, 214-216), lowering blood pressure (namely maintaining the blood pressure at a healthy level, with reference to existing public literature: Research progress on pharmacology of theanine. Ruan Xuelian. *Chinese tea, Thematic review*), assisting in inhibiting tumors and the like. However, due to the short half-life, current oral theanine products need to be taken several times continuously to maintain effective blood drug concentrations, thereby limiting further application of the theanine. At present, there are no relevant reports on how to improve the half-life of the theanine in vivo. Therefore, the development of a safe and efficient method for prolonging the half-life of the theanine has great significance in prolonging the half-life of the theanine in vivo.

SUMMARY

In order to solve the above problems, the present disclosure provides a method for prolonging half-life of theanine in vivo. The method has advantages of cheap and easily available raw materials, mild reaction conditions, a high yield and an application prospect. According to the present disclosure, a theanine glycoside compound is synthesized and obtained by modification of the theanine by using a monosaccharide, which can effectively improve a stability of drugs, improve absorption of drugs in vivo, prolong half-life of drugs, improve bioavailability of drugs and enhance efficacy.

A purpose of the present disclosure is to provide application of a theanine glycoside compound in preparation of a product for prolonging half-life of theanine in vivo. The theanine glycoside compound has a structure shown as follows:

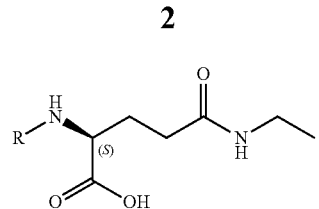

where R is

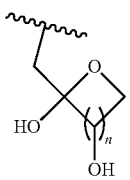

or

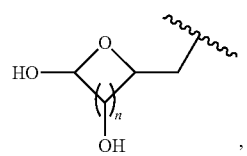

and n is 1-4.

In one embodiment of the present disclosure, the theanine glycoside compound has a main metabolite of the theanine in the blood or brain.

In one embodiment of the present disclosure, the theanine glycoside compound can improve the absorption of the theanine in vivo and prolong the half-life of theanine in the blood and brain.

In one embodiment of the present disclosure, the product may be: an anti-inflammatory product, a product for relieving oxidative damage, an anti-depression product, a product for improving learning and memory abilities, a product for promoting sleep, an antihypertensive product, a product for maintaining the blood pressure at a healthy level, a product for assisting in inhibiting tumors and the like.

In one embodiment of the present disclosure, the product may be a drug, a health care product, a special diet food, a food and the like.

In one embodiment of the present disclosure, the product is an antihypertensive drug, a health care product for assisting in improving memory, or a health care product for promoting sleep or resisting depression.

In one embodiment of the present disclosure, the product may be an oral product.

In one embodiment of the present disclosure, the product may be a liquid product, a solid product or a semi-solid product.

In one embodiment of the present disclosure, when the product containing the theanine glycoside compound of the present disclosure is a pharmaceutical composition, the form thereof may be any one of a solution, a suspension, a powder, a solid molding product and the like and is not particularly limited. Optionally, the product is provided in the form of capsules, tablets, powders, granules, beverages and the like. In addition, the product can be used in combination with other drugs.

In one embodiment of the present disclosure, manufacturing methods of the product of the present disclosure are not particularly limited, including a method of mixing powder of the theanine glycoside compound and other raw materials, a method of dissolving the theanine glycoside compound and other raw materials in a solvent to form a mixed solution, and a method of mixing the theanine glycoside compound and other raw materials. The mixed solution is frozen and subjected to drying, spray drying and other common manufacturing methods of food and drugs. For example, the product can be obtained by mixing components of the theanine glycoside compound with known excipients, carriers, adhesives, stabilizers and the like.

The present disclosure further provides a product for prolonging half-life of theanine in vivo. The product contains one or more theanine glycoside compounds; and the theanine glycoside compound has a structure shown as follows:

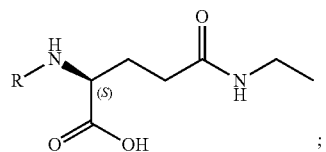

where R is

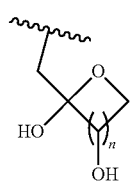

or

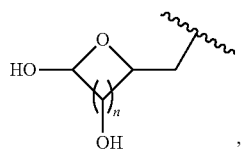

and n is 1-4.

In one embodiment of the present disclosure, the product may be: an anti-inflammatory product, a product for relieving oxidative damage, an anti-depression product, a product for improving learning and memory abilities, a product for promoting sleep, an antihypertensive product, a product for maintaining the blood pressure at a healthy level, a product for assisting in inhibiting tumors and the like.

The present disclosure further provides a method for prolonging half-life of theanine in vivo. The method includes subjecting an amino group in theanine to amination modification by using a monosaccharide, where the monosaccharide is

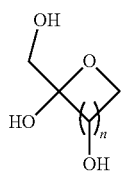

or

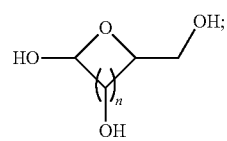

and n is 1-4.

In one embodiment of the present disclosure, the amination modification includes the following processes:

(1) subjecting L-theanine as a substrate to amino protection first to obtain an intermediate 1; then subjecting the intermediate 1 to esterification with an alcohol compound to obtain an intermediate 2; and subjecting the intermediate 2 to deamination protection under an action of an acidizing reagent to obtain an intermediate 3;

(2) subjecting the monosaccharide as a substrate to hydroxyl protection and oxidation to obtain an intermediate 4; and (3) subjecting the intermediate 3 and the intermediate 4 obtained above as a substrate to an amination reduction reaction under an action of a catalyst to obtain an intermediate 5; then subjecting the intermediate 5 to dehydroxylation protection with an acidic reagent to obtain an intermediate 6; and further performing hydrogenation reduction to obtain a target product, namely a theanine glycoside compound.

In one embodiment of the present disclosure, the theanine glycoside compound has a structure shown as follows:

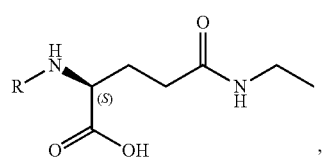

where R is

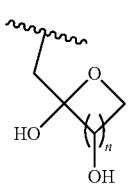

or

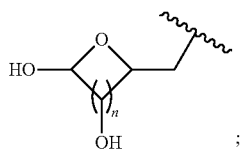

and n is 1-4.

In one embodiment of the present disclosure, the monosaccharide is specifically selected from fructose, galactose and ribose.

In one embodiment of the present disclosure, the R is specifically selected from:

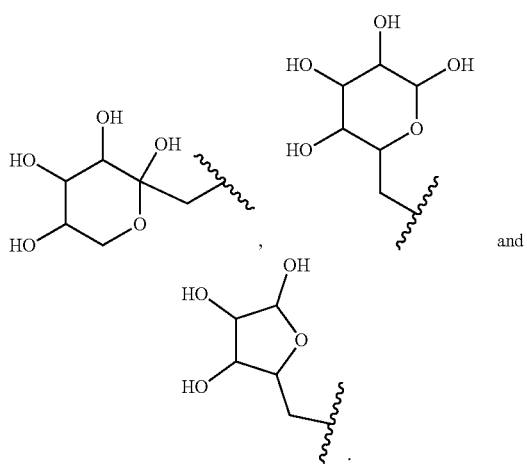

In one embodiment of the present disclosure, in step (1), the amino protection includes reaction processes of:
dissolving the L-theanine, an amino protective reagent and an alkaline reagent in a mixed system of tetrahydrofuran and water, and stirring the compounds at room temperature to carry out a reaction to obtain the intermediate 1.

In one embodiment of the present disclosure, in the process of amino protection in step (1), the amino protective reagent is $Boc_2O$ (di-tert butyl dicarbonate); and a molar ratio of the L-theanine to the amino protective reagent is 1:(1-1.5).

In one embodiment of the present disclosure, in the process of amino protection in step (1), the alkaline reagent is $Na_2CO_3$ or $K_2CO_3$; and a molar ratio of the L-theanine to the alkaline reagent is 1:(2-3).

In one embodiment of the present disclosure, in the process of amino protection in step (1), a volume ratio of the tetrahydrofuran to the water in the mixed system is 1:1; and a concentration of the L-theanine relative to the mixed system is 20 mg/mL-30 mg/mL, specifically 25 mg/mL.

In one embodiment of the present disclosure, in step (1), the esterification includes reaction processes of:
in dichloromethane (DCM) as a solvent, subjecting the obtained intermediate 1 and the alcohol compound to dissolution and an esterification reaction under an action of 1-ethyl-3(3-dimethylpropylamine)carbodiimide (EDCI) and 4-dimethylaminopyridine (DMAP), and stirring the compounds at room temperature to obtain the intermediate 2.

In one embodiment of the present disclosure, in the process of esterification in step (1), the alcohol compound is benzyl alcohol; and a molar ratio of the intermediate 1 to the alcohol compound is 1:(1-1.5).

In one embodiment of the present disclosure, in the process of esterification in step (1), a molar ratio of the intermediate 1 to the EDCI is 1:1.5.

In one embodiment of the present disclosure, in the process of esterification in step (1), a molar ratio of the intermediate 1 to the DMAP is 1:0.1.

In one embodiment of the present disclosure, in the process of esterification in step (1), a concentration of the intermediate 1 relative to the DCM is 20 mg/mL-30 mg/ml, specifically 25 mg/mL.

In one embodiment of the present disclosure, in step (1), the deamination protection includes processes of:
mixing and stirring the intermediate 2, an HCl/dioxane solution and DCM at room temperature to obtain the intermediate 3.

In one embodiment of the present disclosure, in step (2), reaction processes include:
dissolving the monosaccharide in dichloromethane (DCM), and performing stirring in a mixture of dimethyl sulfoxide (DMSO) and oxalyl chloride $(COCl)_2$ as an oxidation system in an environment of $N_2$ at $-50°$ C. to $-70°$ C. for 10 min-40 min to obtain the intermediate 4.

In one embodiment of the present disclosure, a preparation process of the oxidation system specifically includes: dispersing the DMSO in the DCM to obtain a DMSO dispersion solution; dispersing the $(COCl)_2$ in DCM precooled to $-50°$ C. to $-70°$ C. to obtain a $(COCl)_2$ dispersion solution; and then adding the $(COCl)_2$ dispersion solution dropwise into the DMSO dispersion solution in an environment of $N_2$ at $-50°$ C. to $-70°$ C. to obtain the oxidation system.

In one embodiment of the present disclosure, in the oxidation system, a molar ratio of the DMSO to the $(COCl)_2$ is 2:1; a concentration of the DMSO dispersion solution is 0.5 g/mL-1.0 g/mL, specifically 0.75 g/mL; and a concentration of the $(COCl)_2$ dispersion solution is 0.05 g/mL-0.1 g/mL.

In one embodiment of the present disclosure, a molar ratio of the monosaccharide to the $(COCl)_2$ is 1:0.5-1:5, further preferably 1:(1-2).

In one embodiment of the present disclosure, in the amination reduction in step (3), a molar ratio of the intermediate 3 to the intermediate 4 is 1:(0.8-1.5).

In one embodiment of the present disclosure, in the amination reduction in step (3), the catalyst is NaBH$(COOCH_3)_3$.

In one embodiment of the present disclosure, the amination reduction in step (3) is performed in DCM as a solvent, and a concentration of the intermediate 3 relative to the DCM is 20 mg/mL-30 mg/mL.

In one embodiment of the present disclosure, the amination reduction reaction in step (3) is carried out at a temperature of $-50°$ C. to $-70°$ C. for 1 h in a reaction environment of nitrogen.

In one embodiment of the present disclosure, in the dehydroxylation protection in step (3), the acidic reagent is an HCl solution. A concentration of the HCl solution is 5 mol/L.

In one embodiment of the present disclosure, in step (3), the dehydroxylation protection specifically includes processes of: mixing the HCl solution with THF, then adding the intermediate 5, and performing stirring to carry out a reaction. A volume ratio of the HCl to the THF is 1:1.

In one embodiment of the present disclosure, in step (3), the hydrogenation reduction includes dissolving a palladium-carbon catalyst and the intermediate 6 in methanol, introducing hydrogen, and performing stirring at room temperature in an environment of $H_2$ overnight.

In one embodiment of the present disclosure, a use amount of the palladium-carbon catalyst relative to the intermediate 6 in a process of the hydrogenation reduction is 10 wt %.

In one embodiment of the present disclosure, the theanine glycoside compound has a main metabolite of the theanine in the blood or brain.

In one embodiment of the present disclosure, the theanine glycoside compound can improve the absorption of the theanine in vivo and prolong the half-life of the theanine in the blood or brain.

The present disclosure further provides a theanine glycoside compound having a structure shown as follows:

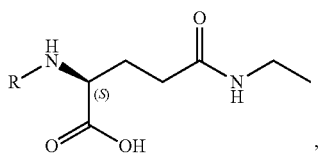

where R is selected from

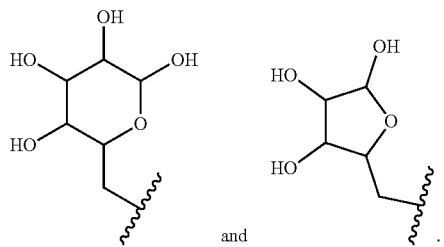 [SMILES: *CC1OC(O)C(O)C(O)C1O ; *CC1OC(O)C(O)C1O]

In one embodiment of the present disclosure, the theanine glycoside compound is prepared by subjecting an amino group in theanine to amination modification by using a monosaccharide, where the monosaccharide is selected from galactose and ribose.

The present disclosure further provides application of a theanine glycoside compound in preparation of drugs for lowering blood pressure.

The present disclosure further provides application of a theanine glycoside compound in preparation of health care products for assisting in improving memory.

The present disclosure further provides application of a theanine glycoside compound in preparation of health care products for promoting sleep and resisting depression.

Beneficial Effects

According to the present disclosure, a theanine glycoside prepared by modification with a specific monosaccharide is used for prolonging half-life of theanine in vivo, which can be used for preparing sustained release drugs, prolonging action time of drugs, reducing administration frequency and improving compliance of patients. The theanine glycoside compound obtained after modification may have a broad application prospect and a high commercial value in scientific research and clinical application.

The theanine itself has many beneficial effects of resisting inflammation, relieving oxidative damage, promoting sedation, resisting depression, improving learning and memory abilities, promoting sleep, lowering blood pressure, assisting in inhibiting tumors and the like. By prolonging the half-life of the theanine in vivo, a theanine glycoside prepared by modification with the specific monosaccharide in the present disclosure can be used for preparing a product for prolonging the half-life of the theanine in vivo, and can better achieve the above beneficial effects of the theanine.

DETAILED DESCRIPTION

Figure 1:
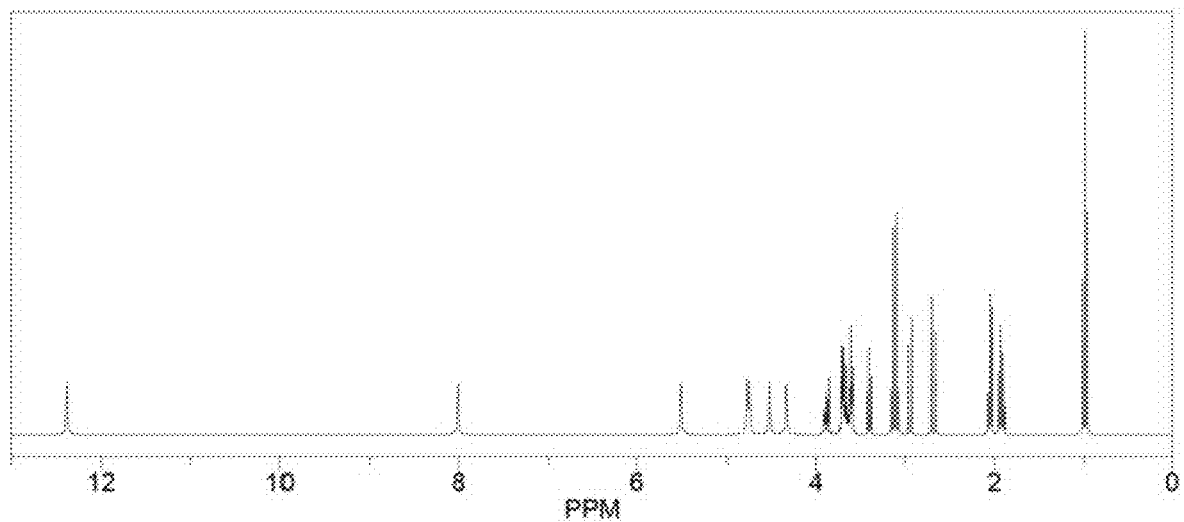
FIG. 1 shows a nuclear magnetic hydrogen spectrum of 1-deoxy-1-L-theanine-D-fructopyranose obtained in Example 1.
Figure 2:
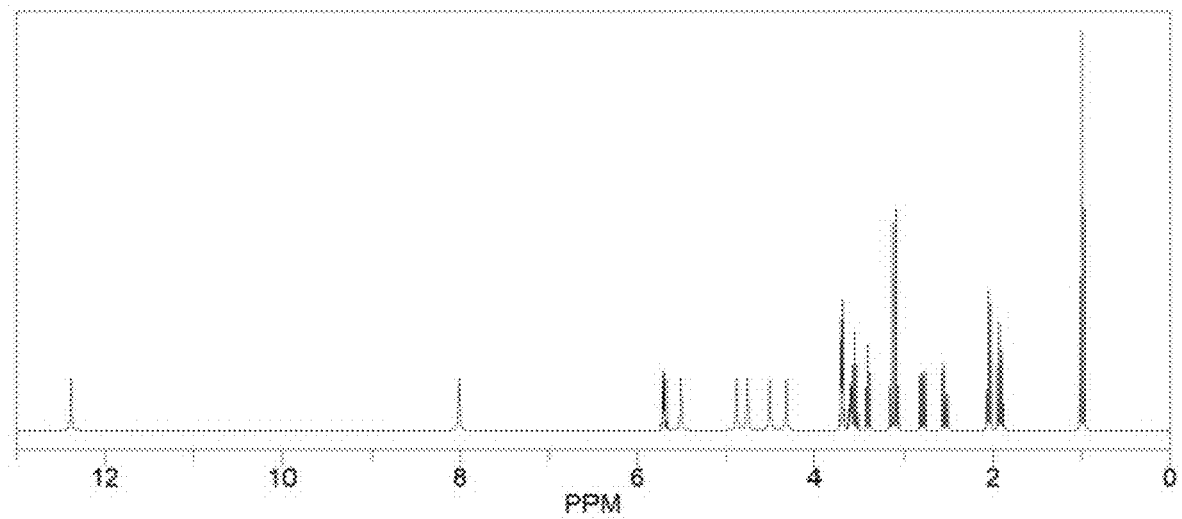
FIG. 2 shows a nuclear magnetic hydrogen spectrum of 1-deoxy-1-L-theanine-D-galactopyranose obtained in Example 2.
Figure 3:
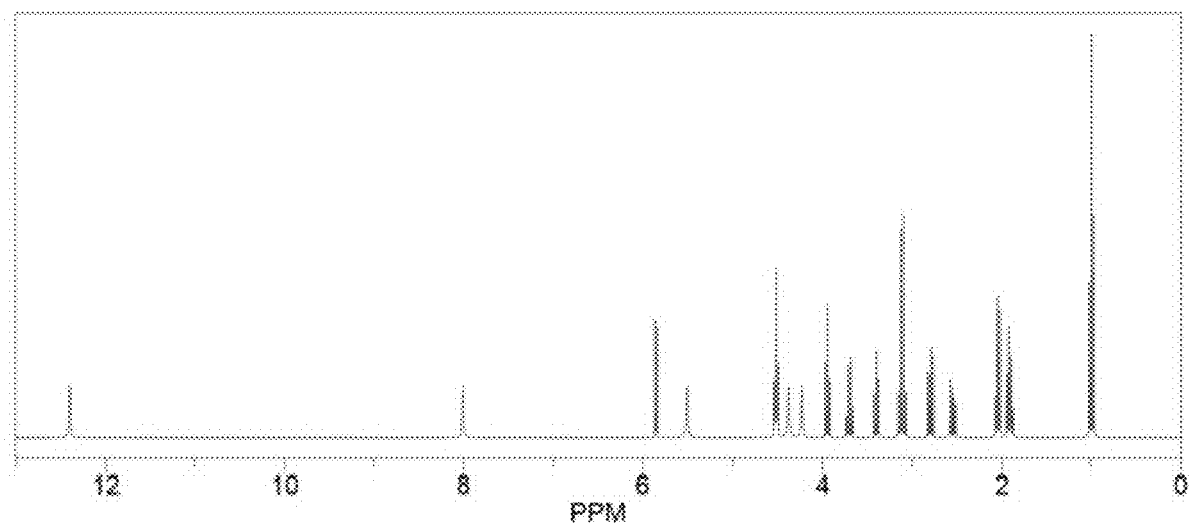
FIG. 3 shows a nuclear magnetic hydrogen spectrum of 1-deoxy-1-L-theanine-D-ribopyranose obtained in Example 3.

Example 1: Method for Prolonging Half-Life of Theanine In Vivo

Synthesis of 1-Deoxy-1-L-Theanine-D-Fructopyranose Based on Theanine:

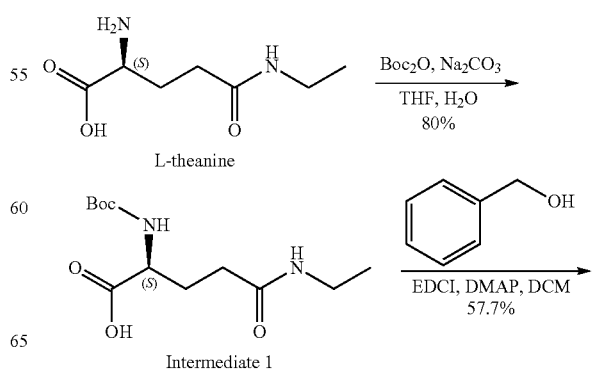

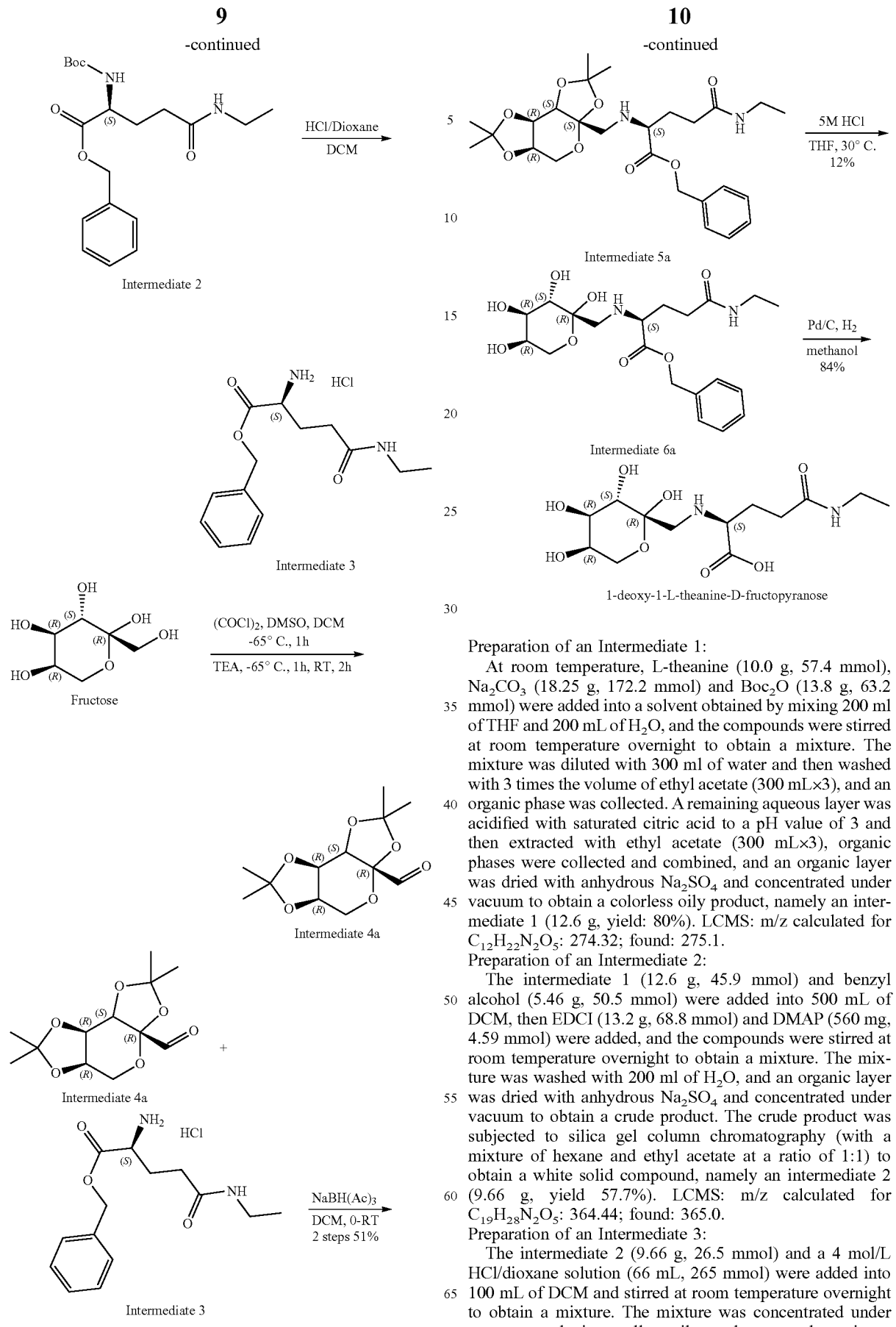

Preparation of an Intermediate 1:

At room temperature, L-theanine (10.0 g, 57.4 mmol), Na$_2$CO$_3$ (18.25 g, 172.2 mmol) and Boc$_2$O (13.8 g, 63.2 mmol) were added into a solvent obtained by mixing 200 ml of THF and 200 mL of H$_2$O, and the compounds were stirred at room temperature overnight to obtain a mixture. The mixture was diluted with 300 ml of water and then washed with 3 times the volume of ethyl acetate (300 mL×3), and an organic phase was collected. A remaining aqueous layer was acidified with saturated citric acid to a pH value of 3 and then extracted with ethyl acetate (300 mL×3), organic phases were collected and combined, and an organic layer was dried with anhydrous Na$_2$SO$_4$ and concentrated under vacuum to obtain a colorless oily product, namely an intermediate 1 (12.6 g, yield: 80%). LCMS: m/z calculated for C$_{12}$H$_{22}$N$_2$O$_5$: 274.32; found: 275.1.

Preparation of an Intermediate 2:

The intermediate 1 (12.6 g, 45.9 mmol) and benzyl alcohol (5.46 g, 50.5 mmol) were added into 500 mL of DCM, then EDCI (13.2 g, 68.8 mmol) and DMAP (560 mg, 4.59 mmol) were added, and the compounds were stirred at room temperature overnight to obtain a mixture. The mixture was washed with 200 ml of H$_2$O, and an organic layer was dried with anhydrous Na$_2$SO$_4$ and concentrated under vacuum to obtain a crude product. The crude product was subjected to silica gel column chromatography (with a mixture of hexane and ethyl acetate at a ratio of 1:1) to obtain a white solid compound, namely an intermediate 2 (9.66 g, yield 57.7%). LCMS: m/z calculated for C$_{19}$H$_{28}$N$_2$O$_5$: 364.44; found: 365.0.

Preparation of an Intermediate 3:

The intermediate 2 (9.66 g, 26.5 mmol) and a 4 mol/L HCl/dioxane solution (66 mL, 265 mmol) were added into 100 mL of DCM and stirred at room temperature overnight to obtain a mixture. The mixture was concentrated under vacuum to obtain a yellow oily product, namely an intermediate 3 (10.45 g, crude oil) without further purification. LCMS: m/z calculated for $C_{14}H_{20}N_2O_3$: 264.33; found: 265.3.

Preparation of an Intermediate 4a:

DMSO (9.0 g, 115.2 mmol) was added into 12 mL of DCM to obtain a DMSO dispersion solution. $(COCl)_2$ (7.3 g, 57.6 mmol) was added into 100 ml of a DCM solution precooled to −60° C. and uniformly mixed to obtain a $(COCl)_2$ dispersion solution. In an environment of $N_2$ at −60° C., the DMSO dispersion solution was added dropwise into the $(COCl)_2$ dispersion solution and stirred for 20 min to obtain an oxidation system.

In an environment of $N_2$ at −60° C., fructose (15.0 g, 83.3 mmol) was dissolved in DCM (66 mL), added dropwise into the oxidation system and stirred for 30 min. In an environment of $N_2$ at −60° C., triethylamine (32 mL, 0.23 mmol) was added dropwise into a mixture solution, stirred for 10 min, slowly heated to room temperature and then placed overnight. A resulting mixture was washed with $H_2O$ (100 mL), 1 mol/L precooled HCl (200 mL) and normal saline (150 mL), respectively, and an organic layer was dried with anhydrous $Na_2SO_4$ and concentrated under vacuum to obtain a brown oily product, namely an intermediate 4a (8.06 g, crude oil) without purification. LCMS: m/z calculated for $C_{12}H_{18}O_6$: 258.11; found: 258.21.

Preparation of an Intermediate 5a by Amination Reduction

The intermediate 3 (7.95 g, 26.7 mmol) and the intermediate 4a (10.24 g, 26.0 mmol) were added into 300 mL of DCM, then $NaBH(COOCH_3)_3$ (17 g, 80.1 mmol) were added, and the compounds were stirred at room temperature overnight to form a mixture. The mixture was washed with $H_2O$ (200 mL), an organic phase was collected, and the organic phase was dried with anhydrous $Na_2SO_4$ and concentrated under vacuum to obtain a crude product. Then, the crude product was purified by silica gel chromatography (with a mixture of n-hexane and ethyl acetate at a ratio of 1:1 to 0:1) to obtain a yellow oily product, namely an intermediate 5a (10.0 g, two-step yield: 51%). LCMS: m/z calculated for $C_{26}H_{38}N_2O_8$: 506.60; found: 507.8.

Preparation of an Intermediate 6a by Dehydroxylation Protection of the Intermediate 5a:

The intermediate 5a (2.0 g, 3.95 mmol) was added into a solution system obtained by mixing a 5 mol/L HCl solution (8 mL, 40 mmol) and THF (8 mL), the solution was stirred at 30° C. for 2 days, and then a mixture was diluted with water (16 mL). An aqueous layer was washed with ethyl ether (20 mL×2) and ethyl acetate (20 mL×2), the pH of the aqueous layer was adjusted with $NaHCO_3$ (3.4 g, 4.0 mmol), the aqueous layer was washed with ethyl acetate (20 mL×2), collected and concentrated, and a residue was purified by silica gel chromatography (with a mixture of DCM, MeOH and 2% $NH_3$/MeOH at a ratio of 10:1:1) to obtain a yellow oily product, namely an intermediate 6a (210 mg, yield: 12%). LCMS: m/z calculated for $C_{20}H_{30}N_2O_8$: 426.46; found: 427.5.

Preparation of a target product 1-deoxy-1-L-theanine-D-fructopyranose by hydrogenation reduction of the intermediate 6a: The intermediate 6a (300 mg, 0.67 mmol) and a palladium-carbon catalyst (10%, 50 mg) were dissolved in methanol (5 mL) and stirred overnight at room temperature in an environment of $H_2$ (hydrogen balloon) for 5 h to obtain a mixture. The mixture was filtered with diatomite and washed with MeOH, and a filtration solution was concentrated under vacuum to obtain a white solid product, namely a theanine glycoside (200 mg, yield: 84%).

Structural characterization of 1-deoxy-1-L-theanine-D-fructopyranose:

HNMR (400 MHZ, $CDCl_3$):δ 4.32 (s, OH), 4.77 (s, OH), 4.74 (s, OH), 4.51 (s, OH), 12.39 (s, OH), 8.01 (s, NH), 5.52 (s, NH), 5.85 (d, CH), 3.88 (dd, CH), 3.6 (t, CH), 3.7 (t, CH), 2.94 (dd, $CH_2$), 3.40 (t, CH), 3.11 (q, $CH_2$), 2.05 (t, $CH_2$), 1.92 (m, $CH_2$), 0.99 (t, $CH_3$).

Example 2: Method for Prolonging Half-Life of Theanine In Vivo

Synthesis of 1-Deoxy-1-L-Theanine-D-Galactopyranose Based on Theanine:

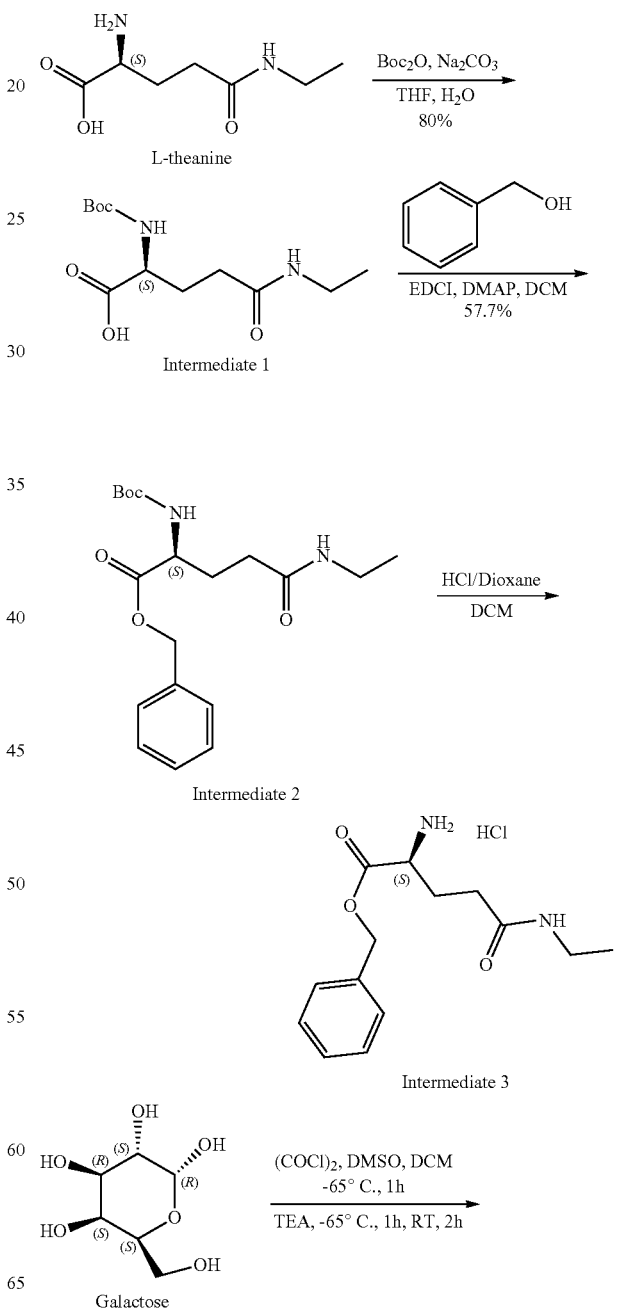

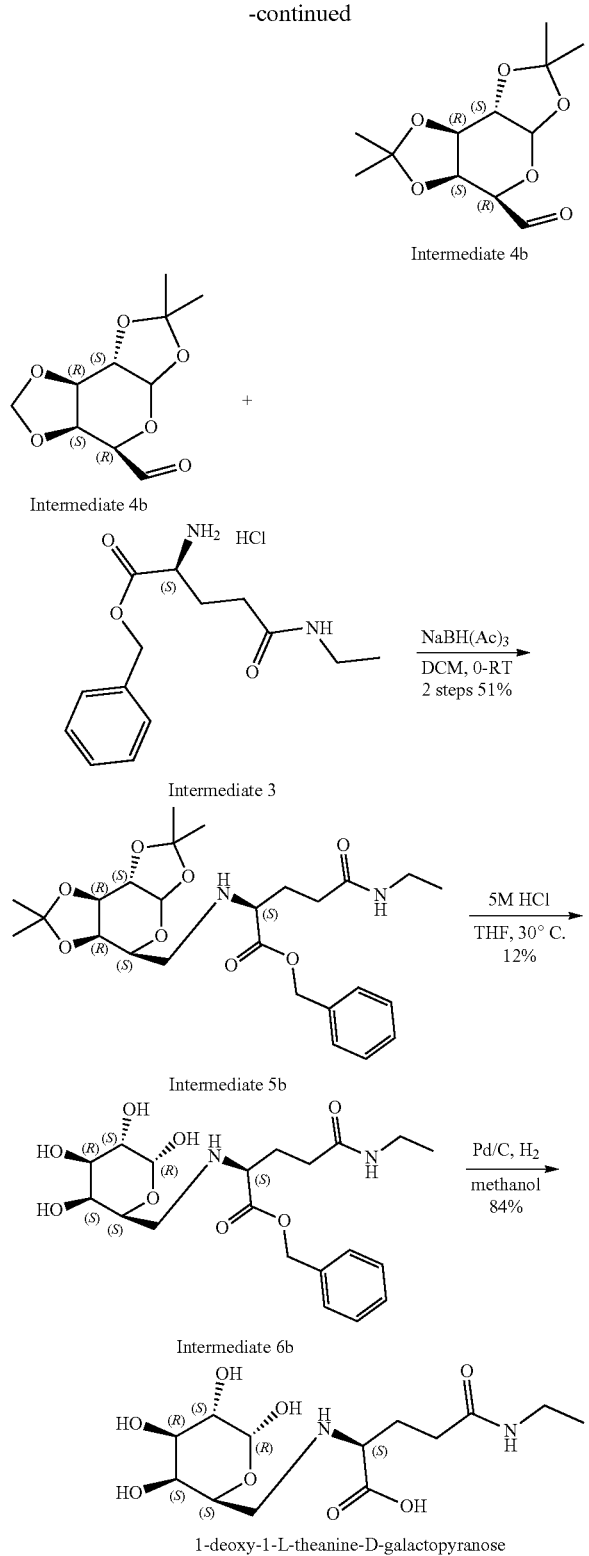

Intermediate 4b

Intermediate 4b

Intermediate 3

Intermediate 5b

Intermediate 6b 1-deoxy-1-L-theanine-D-galactopyranose

Preparation of an Intermediate 1:

At room temperature, L-theanine (10.0 g, 57.4 mmol), Na$_2$CO$_3$ (18.25 g, 172.2 mmol) and Boc$_2$O (13.8 g, 63.2 mmol) were added into a solvent obtained by mixing 200 ml of THF and 200 mL of H$_2$O, and the compounds were stirred at room temperature overnight to obtain a mixture. The mixture was diluted with 300 ml of water and then washed with 3 times the volume of ethyl acetate (300 mL×3), and an organic phase was collected. A remaining aqueous layer was acidified with saturated citric acid to a pH value of 3 and then extracted with ethyl acetate (300 mL×3), organic phases were collected and combined, and an organic layer was dried with anhydrous Na$_2$SO$_4$ and concentrated under vacuum to obtain a colorless oily product, namely an intermediate 1 (12.6 g, yield: 80%). LCMS: m/z calculated for C$_{12}$H$_{22}$N$_2$O$_5$: 274.32; found: 275.1.

Preparation of an Intermediate 2:

The intermediate 1 (12.6 g, 45.9 mmol) and benzyl alcohol (5.46 g, 50.5 mmol) were added into 500 mL of DCM, then EDCI (13.2 g, 68.8 mmol) and DMAP (560 mg, 4.59 mmol) were added, and the compounds were stirred at room temperature overnight to obtain a mixture. The mixture was washed with 200 mL of H$_2$O, and an organic layer was dried with anhydrous Na$_2$SO$_4$ and concentrated under vacuum to obtain a crude product. The crude product was subjected to silica gel column chromatography (with a mixture of hexane and ethyl acetate at a ratio of 1:1) to obtain a white solid compound, namely an intermediate 2 (9.66 g, yield 57.7%). LCMS: m/z calculated for C$_{19}$H$_{28}$N$_2$O$_5$: 364.44; found: 365.0.

Preparation of an Intermediate 3:

The intermediate 2 (9.66 g, 26.5 mmol) and a 4 mol/L HCl/dioxane solution (66 mL, 265 mmol) were added into 100 mL of DCM and stirred at room temperature overnight to obtain a mixture. The mixture was concentrated under vacuum to obtain a yellow oily product, namely an intermediate 3 (10.45 g, crude oil) without further purification. LCMS: m/z calculated for C$_{14}$H$_{20}$N$_2$O$_3$: 264.33; found: 265.3.

Preparation of an Intermediate 4b:

DMSO (9.0 g, 115.2 mmol) was added into 12 mL of DCM to obtain a DMSO dispersion solution. (COCl)$_2$ (7.3 g, 57.6 mmol) was added into 100 ml of a DCM solution precooled to −60° C. and uniformly mixed to obtain a (COCl)$_2$ dispersion solution. In an environment of N$_2$ at −60° C., the DMSO dispersion solution was added dropwise into the (COCl)$_2$ dispersion solution and stirred for 20 min to obtain an oxidation system.

In an environment of N$_2$ at −60° C., galactose (10.0 g, 55.5 mmol) was dissolved in DCM (66 mL), added dropwise into a mixture obtained above and stirred for 30 min. In an environment of N$_2$ at −60° C., triethylamine (32 mL, 0.23 mmol) was added dropwise into a mixture solution, stirred for 10 min, slowly heated to room temperature and then placed overnight. A resulting mixture was washed with H$_2$O (100 mL), 1 mol/L precooled HCl (200 mL) and normal saline (150 mL), respectively, and an organic layer was dried with anhydrous Na$_2$SO$_4$ and concentrated under vacuum to obtain a brown oily product, namely an intermediate 4b (7.88 g, crude oil) without purification. LCMS: m/z calculated for C$_{12}$H$_{18}$O$_6$: 258.11; found: 258.20.

Preparation of an Intermediate 5b by Amination Reduction:

The intermediate 3 (7.95 g, 26.7 mmol) and the intermediate 4b (10.24 g, 26.0 mmol) were added into 300 mL of DCM, then NaBH(COOCH$_3$)$_3$ (17 g, 80.1 mmol) were added, and the compounds were stirred at room temperature overnight to form a mixture. The mixture was washed with H$_2$O (200 mL), an organic phase was collected, and the organic phase was dried with anhydrous Na$_2$SO$_4$ and concentrated under vacuum to obtain a crude product. Then, the crude product was purified by silica gel chromatography (with a mixture of n-hexane and ethyl acetate at a ratio of 1:1 to 0:1) to obtain a yellow oily product, namely an intermediate 5b (9.82 g, two-step yield: 49.5%).

LCMS: m/z calculated for $C_{26}H_{38}N_2O_8$: 506.60; found: 507.8.

Preparation of an Intermediate 6b by Dehydroxylation Protection of the Intermediate 5b:

The intermediate 5b (2.0 g, 3.95 mmol) was added into a solution system obtained by mixing a 5 mol/L HCl solution (8 mL, 40 mmol) and THF (8 mL), the solution was stirred at 30° C. for 2 days, and then a mixture was diluted with water (16 mL). An aqueous layer was washed with ethyl ether (20 mL×2) and ethyl acetate (20 mL×2), the pH of the aqueous layer was adjusted with $NaHCO_3$ (3.4 g, 4.0 mmol), the aqueous layer was washed with ethyl acetate (20 mL×2), collected and concentrated, and a residue was purified by silica gel chromatography (with a mixture of DCM, MeOH and 2% $NH_3$/MeOH at a ratio of 10:1:1) to obtain a yellow oily product, namely an intermediate 6b (180 mg, yield: 11%).

LCMS: m/z calculated for $C_{20}H_{30}N_2O_8$: 426.46; found: 427.5.

Preparation of a Target Product 1-deoxy-1-L-theanine-D-galactopyranose by Hydrogenation Reduction of the Intermediate 6b:

The intermediate 6b (300 mg, 0.67 mmol) and a palladium-carbon catalyst (10%, 50 mg) were dissolved in methanol (5 mL) and stirred overnight at room temperature in an environment of $H_2$ (hydrogen balloon) for 5 h to obtain a mixture. The mixture was filtered with diatomite and washed with MeOH, and a filtration solution was concentrated under vacuum to obtain a white solid product, namely a theanine glycoside (177 mg, yield: 79.5%).

Structural characterization of 1-deoxy-1-L-theanine-D-galactopyranose:

HNMR (400 MHZ, $CDCl_3$):δ 4.32 (s, OH), 4.77 (s, OH), 4.88 (s, OH), 4.51 (s, OH), 12.39 (s, OH), 8.01 (s, NH), 5.52 (s, NH), 5.70 (m, CH), 3.55 (m, CH), 3.70 (m, CH), 3.60 (m, CH), 3.70 (m, CH), 2.79, 2.53500 (dd, $CH_2$), 3.40 (dd, CH), 3.11 (q, $CH_2$), 2.05 (t, $CH_2$), 1.92 (dd, $CH_2$), 0.99 (t, $CH_3$).

Example 3: Method for Prolonging Half-Life of Theanine In Vivo

Synthesis of 1-Deoxy-1-L-Theanine-D-Ribopyranose Based on Theanine:

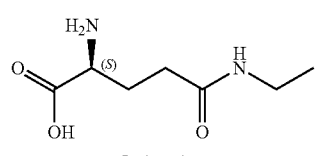
L-theanine

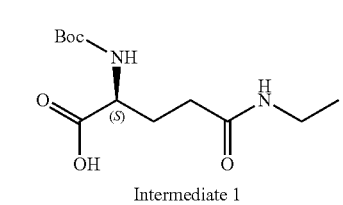
Intermediate 1

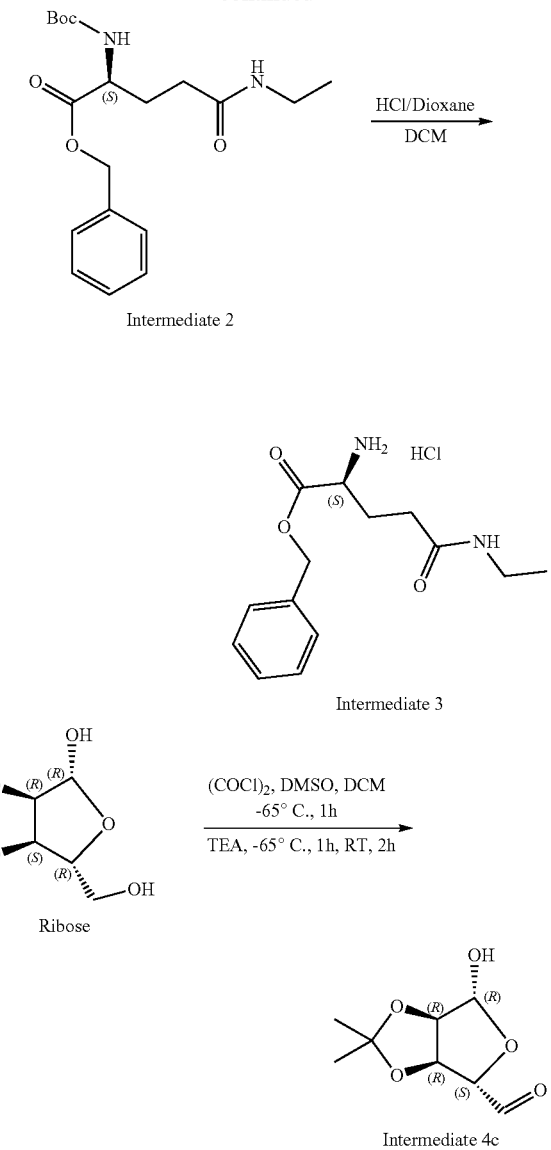

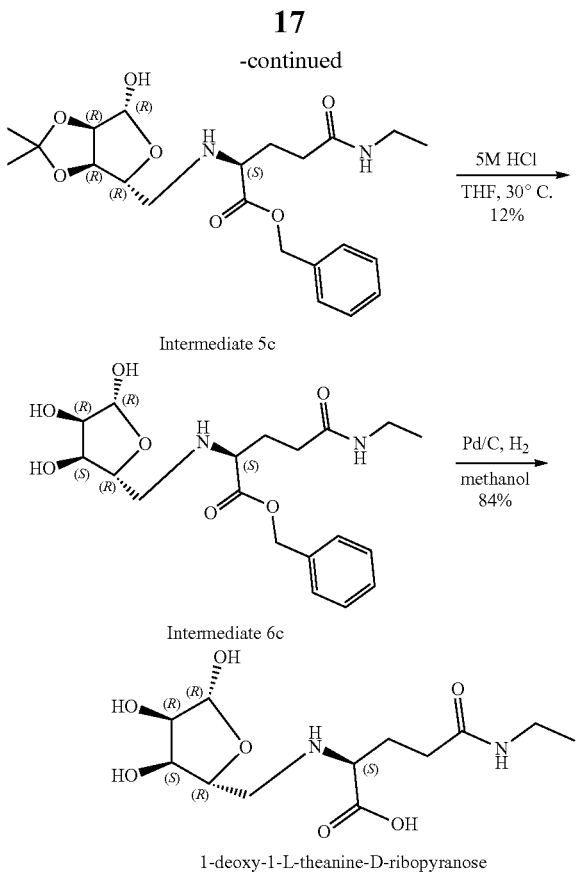

Intermediate 5c

Intermediate 6c 1-deoxy-1-L-theanine-D-ribopyranose

Preparation of an Intermediate 1:

At room temperature, L-theanine (10.0 g, 57.4 mmol), Na$_2$CO$_3$ (18.25 g, 172.2 mmol) and Boc$_2$O (13.8 g, 63.2 mmol) were added into a solvent obtained by mixing 200 ml of THF and 200 mL of H$_2$O, and the compounds were stirred at room temperature overnight to obtain a mixture. The mixture was diluted with 300 ml of water and then washed with 3 times the volume of ethyl acetate (300 mL×3), and an organic phase was collected. A remaining aqueous layer was acidified with saturated citric acid to a pH value of 3 and then extracted with ethyl acetate (300 mL×3), organic phases were collected and combined, and an organic layer was dried with anhydrous Na$_2$SO$_4$ and concentrated under vacuum to obtain a colorless oily product, namely an intermediate 1 (12.6 g, yield: 80%). LCMS: m/z calculated for C$_{12}$H$_{22}$N$_2$O$_5$: 274.32; found: 275.1.

Preparation of an Intermediate 2:

The intermediate 1 (12.6 g, 45.9 mmol) and benzyl alcohol (5.46 g, 50.5 mmol) were added into 500 mL of DCM, then EDCI (13.2 g, 68.8 mmol) and DMAP (560 mg, 4.59 mmol) were added, and the compounds were stirred at room temperature overnight to obtain a mixture. The mixture was washed with 200 mL of H$_2$O, and an organic layer was dried with anhydrous Na$_2$SO$_4$ and concentrated under vacuum to obtain a crude product. The crude product was subjected to silica gel column chromatography (with a mixture of hexane and ethyl acetate at a ratio of 1:1) to obtain a white solid compound, namely an intermediate 2 (9.66 g, yield 57.7%). LCMS: m/z calculated for C$_{19}$H$_{28}$N$_2$O$_5$: 364.44; found: 365.0.

Preparation of an Intermediate 3:

The intermediate 2 (9.66 g, 26.5 mmol) and a 4 mol/L HCl/dioxane solution (66 mL, 265 mmol) were added into 100 ml of DCM and stirred at room temperature overnight to obtain a mixture. The mixture was concentrated under vacuum to obtain a yellow oily product, namely an intermediate 3 (10.45 g, crude oil) without further purification. LCMS: m/z calculated for C$_{14}$H$_{20}$N$_2$O$_3$: 264.33; found: 265.3.

Preparation of an Intermediate 4c:

DMSO (9.0 g, 115.2 mmol) was added into 12 mL of DCM to obtain a DMSO dispersion solution. (COCl)$_2$ (7.3 g, 57.6 mmol) was added into 100 ml of a DCM solution precooled to −60° C. and uniformly mixed to obtain a (COCl)$_2$ dispersion solution. In an environment of N$_2$ at −60° C., the DMSO dispersion solution was added dropwise into the (COCl)$_2$ dispersion solution and stirred for 20 min to obtain an oxidation system.

In an environment of N$_2$ at −60° C., ribose (15.0 g, 99.9 mmol) was dissolved in DCM (66 mL), added dropwise into a mixture obtained above and stirred for 30 min. In an environment of N$_2$ at −60° C., triethylamine (32 mL, 0.23 mmol) was added dropwise into a mixture solution, stirred for 10 min, slowly heated to room temperature and then placed overnight. A resulting mixture was washed with H$_2$O (100 mL), 1 mol/L precooled HCl (200 mL) and normal saline (150 mL), respectively, and an organic layer was dried with anhydrous Na$_2$SO$_4$ and concentrated under vacuum to obtain a brown oily product, namely an intermediate 4c (7.55 g, crude oil) without purification. LCMS: m/z calculated for C$_8$H$_{12}$O$_5$: 188.07; found: 188.15.

Preparation of an Intermediate 5c by Amination Reduction:

The intermediate 3 (7.95 g, 26.7 mmol) and the intermediate 4c (14.46 g, 26.0 mmol) were added into 300 mL of DCM, then NaBH(COOCH$_3$)$_3$ (17 g, 80.1 mmol) were added, and the compounds were stirred at room temperature overnight to form a mixture. The mixture was washed with H$_2$O (200 mL), an organic phase was collected, and the organic phase was dried with anhydrous Na$_2$SO$_4$ and concentrated under vacuum to obtain a crude product. Then, the crude product was purified by silica gel chromatography (with a mixture of n-hexane and ethyl acetate at a ratio of 1:1 to 0:1) to obtain a yellow oily product, namely an intermediate 5c (9.66 g, two-step yield: 48.7%). LCMS: m/z calculated for C$_{22}$H$_{32}$N$_2$O$_7$: 436.22; found: 436.32.

Preparation of an Intermediate 6c by Dehydroxylation Protection of the Intermediate 5c:

The intermediate 5c (2.0 g, 3.95 mmol) was added into a solution system obtained by mixing a 5 mol/L HCl solution (8 mL, 40 mmol) and THF (8 mL), the solution was stirred at 30° C. for 2 days, and then a mixture was diluted with water (16 mL). An aqueous layer was washed with ethyl ether (20 mL×2) and ethyl acetate (20 mL×2), the pH of the aqueous layer was adjusted with NaHCO$_3$ (3.4 g, 4.0 mmol), the aqueous layer was washed with ethyl acetate (20 mL×2), collected and concentrated, and a residue was purified by silica gel chromatography (with a mixture of DCM, MeOH and 2% NH$_3$/MeOH at a ratio of 10:1:1) to obtain a yellow oily product, namely an intermediate 6c (178 mg, yield: 10.8%). LCMS: m/z calculated for C$_{19}$H$_{28}$N$_2$O$_7$: 396.44; found: 396.22.

Preparation of a Target Product 1-deoxy-1-L-theanine-D-ribopyranose by Hydrogenation Reduction of the Intermediate 6c:

The intermediate 6c (300 mg, 0.67 mmol) and a palladium-carbon catalyst (10%, 50 mg) were dissolved in methanol (5 mL) and stirred overnight at room temperature in an environment of H$_2$ (hydrogen balloon) for 5 h to obtain a mixture. The mixture was filtered with diatomite and washed with MeOH, and a filtration solution was concentrated under vacuum to obtain a white solid product, namely a theanine glycoside (191 mg, yield: 80.2%).

Structural characterization of 1-deoxy-1-L-theanine-D-ribopyranose:

HNMR (400 MHZ, CDCl$_3$):δ 4.22 (s, OH), 4.37 (s, OH), 4.51 (s, OH), 12.39 (s, OH), 8.01 (s, NH), 5.52 (s, NH), 5.85 (d, CH), 3.70 (dd, CH), 3.95 (t, CH), 4.51 (t, CH), 2.79, 2.53 (dd, CH$_2$), 3.40 (t, CH), 3.11 (q, CH$_2$), 2.05 (t, CH$_2$), 1.92 (m, CH$_2$), 0.99 (t, CH$_3$).

Example 4: Testing of Metabolites of Theanine Glycosidation Derivatives In Vivo 1-deoxy-1-L-theanine-D-fructopyranose was recorded as a theanine glycoside 1, 1-deoxy-1-L-theanine-D-galactopyranose was recorded as a theanine glycoside 2, and 1-deoxy-1-L-theanine-D-ribopyranose was recorded as a theanine glycoside 3.

1. Experimental animals: Male C57BL/6J mice with the body weight of (20±2) g were used.
2. Administration and sample collection: The mice were intragastrically administered with theanine glucosides (n=6), which were subjected to fasting without limitation of water for 12 h before administration and then allowed to drink water after intragastric administration. The intragastric administration dose was 500 mg/kg. 1 h after the administration, eyeballs of 6 mice in each group were removed, and 0.5 mL of blood was collected. The mice were killed by cervical dislocation and then dissected to obtain brain tissues, blood samples were centrifuged at 3,000 g for 15 min, supernatants were separated to obtain plasma samples, and the plasma samples were stored at −80° C. for subsequent detection.
3. Instrument conditions and determination of plasma samples:

Instrument: SCIEX Triple Quad™ 5500 LC-MS/MS was used.

Treatment of the samples: 1.5 ml of a 70% methanol aqueous solution was added into 100 μL of the plasma samples and 20 mg of the brain tissues and mixed in vortex for 30 s, respectively, and a resulting mixture was subjected to ultrasonic treatment in an ice water bath for 10 min, followed by standing at −20° C. for 20 min to precipitate a protein. The protein was centrifuged briefly for 15 s for 2 times, a supernatant was taken out, dried by a vacuum concentrator at 4° C., redissolved with 200 μl of methanol and centrifuged at 4° C. at 12,000 g for 15 min, and 100 μL of the supernatant was taken for LC-MS/MS analysis.

Figure 4:
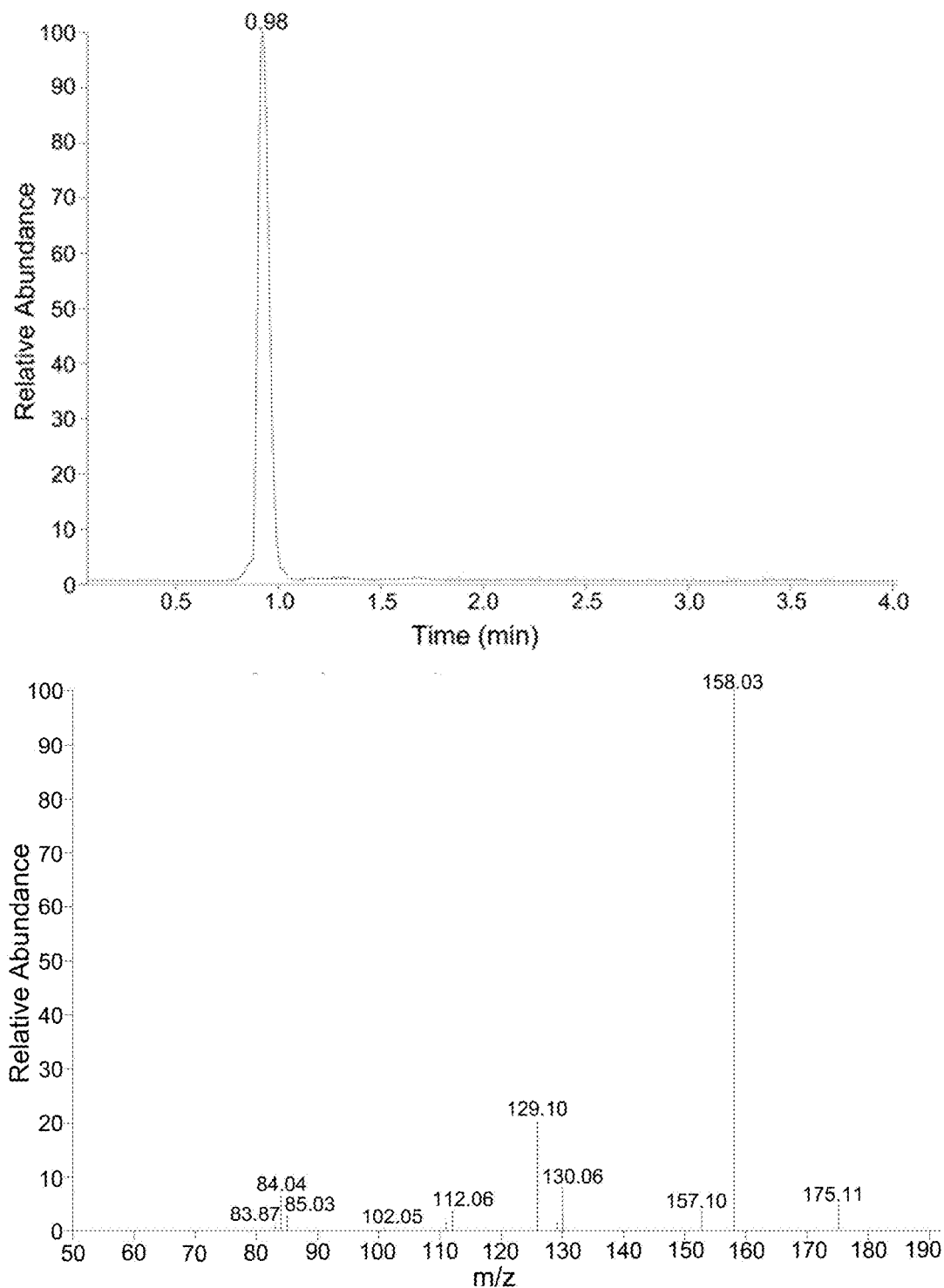
FIG. 4 shows a liquid chromatogram and a corresponding mass spectrogram of metabolites of theanine glycosidation derivatives in vivo in Example 4.
Figure 5:
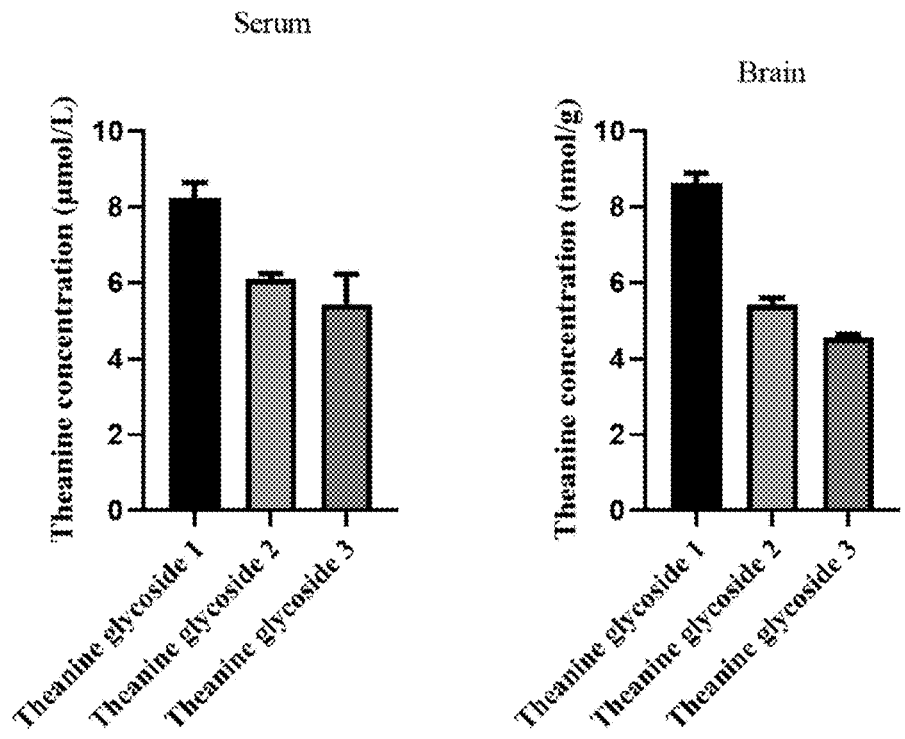
FIG. 5 shows comparison of contents of theanine obtained by metabolism of various theanine glycosidation derivatives in the blood and the brain in Example 4.

4. Experimental results:

A liquid chromatogram and a corresponding mass spectrogram are shown in FIG. 4. Corresponding contents of theanine obtained by metabolism of various theanine glycosidation derivatives in the blood and the brain are shown in FIG. 5. The results show that after intragastric administration in the mice, the theanine glycosidation derivatives have a main metabolite of theanine in the blood and the brain in vivo.

Example 5: Determination of Pharmacokinetics of Theanine Produced by Metabolism of Theanine Glycosidation Derivatives in the Blood 1-deoxy-1-L-theanine-D-fructopyranose was recorded as a theanine glycoside 1, 1-deoxy-1-L-theanine-D-galactopyranose was recorded as a theanine glycoside 2, and 1-deoxy-1-L-theanine-D-ribopyranose was recorded as a theanine glycoside 3.

1. Experimental animals: Male SD rats with the body weight of (180±20) g were used.
2. Administration and sample collection: The rats were intragastrically administered (n=6), which were randomly divided into two groups, including a theanine group and a theanine glycoside group. The rats were subjected to fasting without limitation of water for 12 h before administration and then allowed to drink water after intragastric administration. The intragastric administration dose was 500 mg/kg. 1 h, 2 h, 4 h, 8 h and 12 h before and after the administration, 0.5 mL of blood was collected from eye sockets of 6 rats in each group, respectively. Blood samples were centrifuged at 3,000 g for 15 min, supernatants were separated to obtain plasma samples, and the plasma samples were stored at −80° C.
3. Instrument conditions and determination of plasma samples:

Instrument: SCIEX Triple Quad™ 5500 LC-MS/MS was used.

Drawing of a standard curve: 100 μL of blank plasma of the rats was taken, added into 1.5 mL of a 70% methanol aqueous solution and mixed in vortex for 30 s, and a resulting mixture was subjected to ultrasonic treatment in an ice water bath for 10 min, followed by standing at −20° C. for 20 min to precipitate a protein. The protein was centrifuged briefly for 15 s for 2 times, and a supernatant was taken out, dried by a vacuum concentrator at 4° C. and redissolved with 200 μl of methanol. 200 μL of a series of standard solutions of a tested compound and 10 μL of an internal standard (DL-4-chlorophenylmethylamino) were sequentially added to prepare plasma samples of the tested compound with a plasma concentration of 0.1 μM, 1 μM, 10 μM, 100 μM, 1,000 μM and 10,000 μM respectively, followed by LC-MS/MS analysis. With the concentration of the tested compound (x) as the abscissa and the ratio of peak areas of the tested compound and the internal standard (y) as the ordinate, regression calculation was performed by a weighted least square method to obtain a linear regression equation, namely a standard curve. According to the standard curve, the linear range of the tested compound in the plasma of the rats was 0.1 μM-10,000 μM as determined by an LC-MS/MS method.

Treatment of the plasma samples: 1.5 mL of a 70% methanol aqueous solution was added into 100 μL of the plasma samples of the rats and mixed in vortex for 30 s, and a resulting mixture was subjected to ultrasonic treatment in an ice water bath for 10 min, followed by standing at −20° C. for 20 min to precipitate a protein. The protein was centrifuged briefly for 15 s for 2 times, a supernatant was taken out, dried by a vacuum concentrator at 4° C., redissolved with 200 μL of methanol and centrifuged at 4° C. at 12,000 g for 15 min, and 100 μL of the supernatant was taken for LC-MS/MS analysis.

The half-life $T_{1/2}$ was calculated according to formulas below:

$$k = \frac{\ln C0 - \ln C}{t}, T1/2 = \frac{\ln 2}{k},$$

where k is an elimination rate constant, C0 and C are drug concentrations at two time points, and t is a time difference between C and C0.

Figure 6:
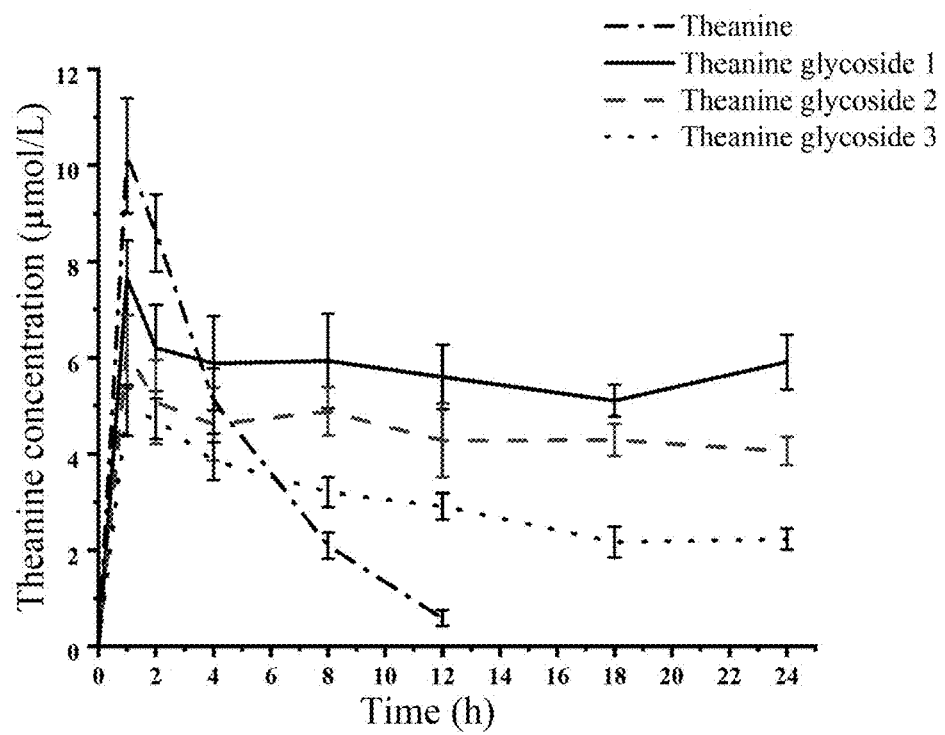
FIG. 6 shows concentration changes of theanine produced by intragastric administration of theanine glycosides in the blood in Example 5.
Figure 7:
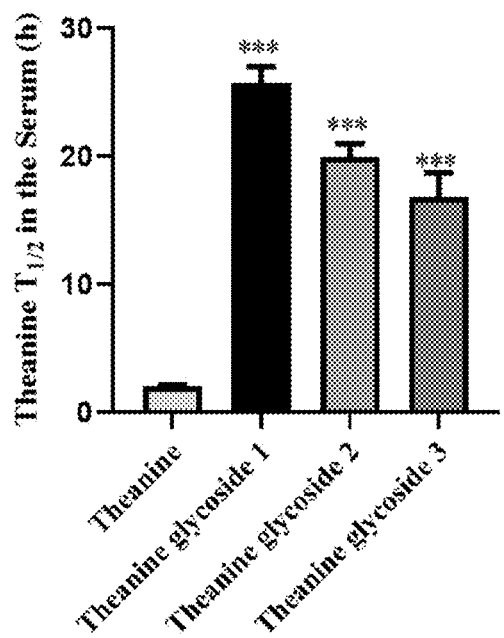
FIG. 7 shows pharmacokinetic results of theanine and different theanine glycosides in the blood in Example 5.

4. Experimental results:

Concentration changes of theanine produced by intragastric administration of theanine glycosides in the blood are shown in FIG. 6, and corresponding pharmacokinetic results are shown in Table 1 and FIG. 7.

TABLE 1

Half-life results of theanine and different theanine glycosides in the blood

| | $T_{1/2}$ (h) |
|---|---|
| Theanine | 2.05 ± 0.12 |
| Theanine glycoside 1 | 25.70 ± 1.31 |
| Theanine glycoside 2 | 19.94 ± 1.06 |
| Theanine glycoside 3 | 16.80 ± 1.93 |

Example 6: Determination of Pharmacokinetics of Theanine Produced by Metabolism of Theanine Glycosidation Derivatives in the Brain 1-deoxy-1-L-theanine-D-fructopyranose was recorded as a theanine glycoside 1, 1-deoxy-1-L-theanine-D-galactopyranose was recorded as a theanine glycoside 2, and 1-deoxy-1-L-theanine-D-ribopyranose was recorded as a theanine glycoside 3.

1. Experimental animals: Male C57BL/6J mice with the body weight of (20±2) g were used.
2. Administration and sample collection: The mice were intragastrically administered (n=6), which were randomly divided into two groups, including a theanine group and a theanine glycoside group. The mice were subjected to fasting without limitation of water for 12 h before administration and then allowed to drink water after intragastric administration. The intragastric administration dose was 500 mg/kg. 1 h, 2 h, 4 h, 8 h and 12 h before and after the administration, 6 mice in each group were killed by cervical dislocation and then dissected to obtain brain tissues respectively, and the brain tissues were stored at −80° C. for subsequent detection.
3. Instrument conditions and determination of brain tissue samples:

Instrument: SCIEX Triple Quad™ 5500 LC-MS/MS was used.

Drawing of a standard curve: 20 mg of blank brain tissues of the mice were taken, added into 1.5 mL of a 70% methanol aqueous solution and mixed in vortex for 30 s, and a resulting mixture was subjected to ultrasonic treatment in an ice water bath for 10 min, followed by standing at −20° C. for 20 min to precipitate a protein. The protein was centrifuged briefly for 15 s for 2 times, and a supernatant was taken out, dried by a vacuum concentrator at 4° C. and redissolved with 200 μL of methanol. 200 μl of a series of standard solutions of a tested compound and 10 μl of an internal standard (DL-4-chlorophenylmethylamino) were sequentially added to prepare brain tissue samples of the tested compound with a brain tissue concentration of 0.1 μM, 1 μM, 10 μM, 100 μM, 1,000 μM and 10,000 μM respectively, followed by LC-MS/MS analysis. With the concentration of the tested compound (x) as the abscissa and the ratio of peak areas of the tested compound and the internal standard (y) as the ordinate, regression calculation was performed by a weighted least square method to obtain a linear regression equation, namely a standard curve. According to the standard curve, the linear range of the tested compound in the plasma of the mice was 0.1 μM-10,000 μM as determined by an LC/MS/MS method.

Treatment of the brain tissue samples: The brain tissues with a mass of 20±2 mg were precisely weighed and added into a 2 mL EP tube, a 70% methanol aqueous solution was added at 20 mg/1.5 mL, homogenized by a freezing grinder at a low temperature of 4° C. and mixed in vortex for 30 s, and a resulting mixture was subjected to ultrasonic treatment in an ice water bath for 10 min, followed by standing at −20° C. for 20 min to precipitate a protein. The protein was centrifuged briefly for 15 s for 2 times, a supernatant was taken out, dried by a vacuum concentrator at 4° C., redissolved with 200 μL of methanol and centrifuged at 4° C. at 12,000 g for 15 min, and 100 μL of the supernatant was taken for LC-MS/MS analysis.

Figure 8:
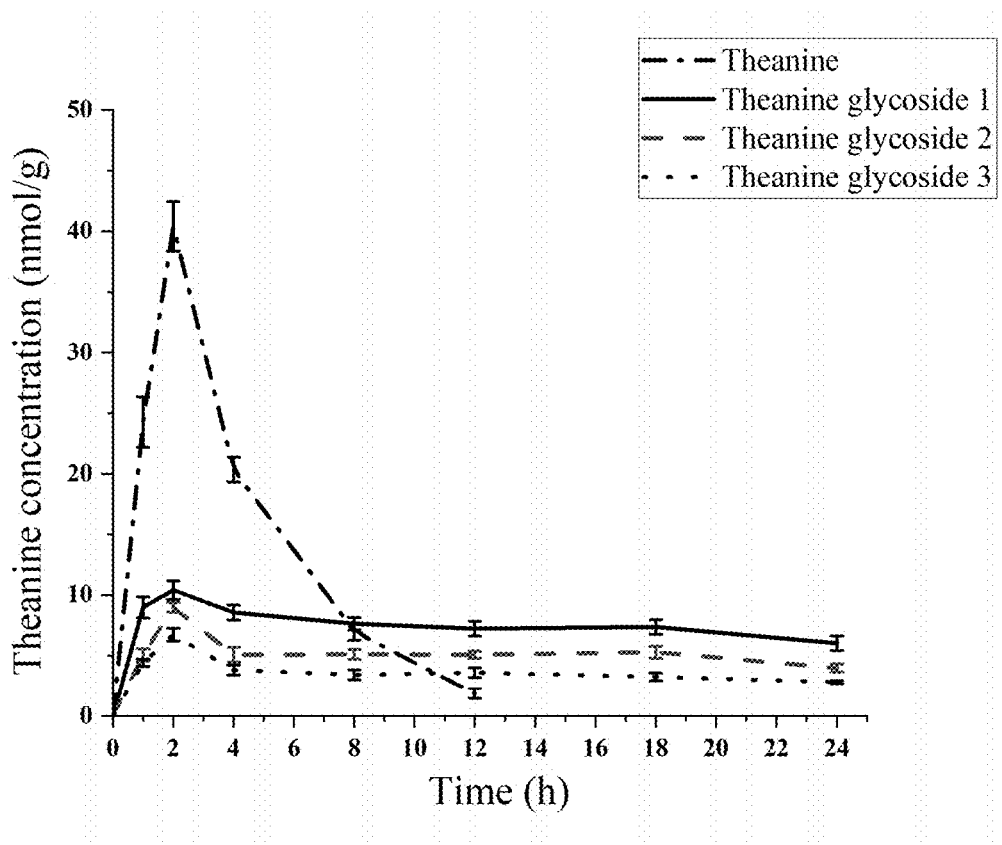
FIG. 8 shows concentration changes of theanine produced by intragastric administration of theanine glycosides in the brain in Example 6.
Figure 9:
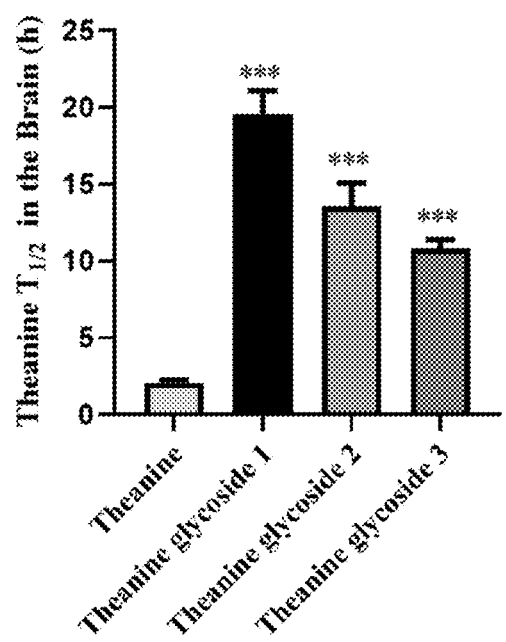
FIG. 9 shows pharmacokinetic results of theanine and different theanine glycosides in the brain in Example 6.

4. Experimental results:

Concentration changes of theanine produced by intragastric administration of theanine glycosides in the brain are shown in FIG. 8, and corresponding pharmacokinetic results are shown in Table 2 and FIG. 9.

TABLE 2

Half-life results of theanine and different theanine glycosides in the brain

| | $T_{1/2}$ (h) |
|---|---|
| Theanine | 2.07 ± 0.19 |
| Theanine glycoside 1 | 19.56 ± 1.54 |
| Theanine glycoside 2 | 13.55 ± 1.55 |
| Theanine glycoside 3 | 10.85 ± 0.54 |

Example 7: Application of a Theanine Glycoside Compound in Preparation of a Product for Prolonging Half-Life of Theanine In Vivo Application of a theanine glycoside compound in preparation of a product for prolonging half-life of theanine in vivo is provided, where the theanine glycoside compound has a structure shown as follows:

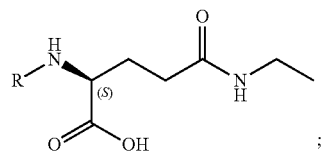

where R is

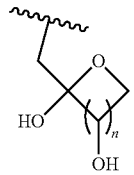

or

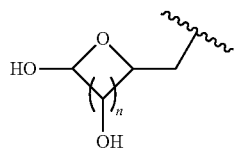

and n is 1-4.

The product may be obtained by replacing theanine partially or completely with any one or more of the theanine glycoside compounds on the basis of any known public formulation or product containing theanine.

The theanine glycoside compound has a main metabolite of theanine in the blood and brain, which can improve the absorption of theanine in vivo and prolong the half-life of theanine in the blood and brain.

Optionally, the product may be: an anti-inflammatory product, a product for relieving oxidative damage, an antidepression product, a product for improving learning and memory abilities, a product for promoting sleep, an antihypertensive product, a product for maintaining the blood pressure at a healthy level, a product for assisting in inhibiting tumors and the like.

In this example, the theanine in any one of existing products may be partially or completely replaced with the theanine glycoside compound, and other improvements may be, but not necessarily, performed on existing public products. The product in this example achieves desired effects based on the fact that the theanine glycoside compound in the product is found for the first time to have the function of prolonging the half-life of theanine in the blood and brain, and the theanine has been found to have corresponding functions of existing public products, such as resisting inflammation, relieving oxidative damage, promoting sedation, resisting depression, improving learning and memory abilities, promoting sleep, reducing blood pressure, assisting in inhibiting tumors and the like.

Example 8: Preparation of a Product for Prolonging Half-Life of Theanine In Vivo from a Theanine Glycoside Compound This example provides application of a theanine glycoside compound in preparation of a product for prolonging half-life of theanine in vivo. The product for prolonging half-life of theanine in vivo is a sleep promoting composition containing a theanine glycoside compound; and the theanine glycoside compound has a structure shown as follows:

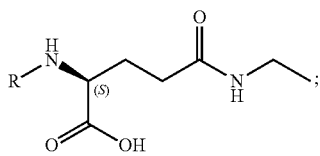

where R is

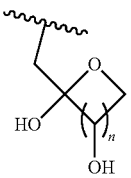

or

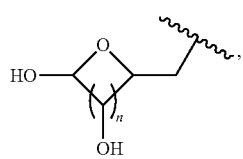

and n is 1-4.

Optionally, the theanine glycoside compound may be any one or more of 1-deoxy-1-L-theanine-D-fructopyranose, 1-deoxy-1-L-theanine-D-galactopyranose and 1-deoxy-1-L-theanine-D-ribopyranose.

At present, use of theanine in preparation of food or drugs for promoting sleep of individuals with sleep disorders has been reported (CN100374108C (sleep promoting composition)). In this example, the theanine in food or drugs for promoting sleep of individuals with sleep disorders may be partially or completely replaced with the theanine glycoside compound, and other improvements may be, but not necessarily, performed on existing food or drugs.

This example provides a sleep promoting composition containing the theanine glycoside compound; or on the basis of the sleep promoting composition, a food or drug suitable for individuals with sleep disorders is also contained.

The sleep promoting composition in this example (hereinafter referred to as composition) can be used in daily life to relieve or alleviate various sleep disorders caused by various reasons. The composition in this example achieves desired effects based on the fact that the theanine glycoside compound in the composition is found for the first time to have the function of prolonging the half-life of theanine in the blood and brain, and the theanine has been found to have a sleep promoting effect.

The content of the theanine glycoside compound in the composition of this example is not particularly limited, which may be appropriately adjusted as required. For example, the appropriate content of the theanine glycoside compound in the composition is preferably 5-100 wt %, particularly preferably 50-100 wt %.

The composition of this example may additionally contain various minerals. In particular, the composition containing minerals is preferably a composition capable of achieving the effect of supplementing essential elements and trace essential elements that are easily deficient in organisms. The content of minerals in the composition is preferably, for example, 0.0001-99.9 wt %, more preferably 0.01-99.9 wt %. The minerals may include iron, magnesium, copper, zinc, selenium, calcium, potassium, manganese, chromium, iodine, molybdenum, nickel, vanadium and other metals necessary to maintain and regulate the stability of organisms or salts of these metals. These substances may be used alone, or used by mixing two or more of them.

In addition, natural drugs, herbs, amino acids, vitamins and the like may also be contained. The contained natural drugs are not particularly limited, preferably including

*Ganoderma lucidum, Rehmannia glutinosa*, Fructus Ziziphi Jujubae and the like that are effective in stabilizing the spirit. In addition, the herbs are not particularly limited, including, for example, fennel, carrot seeds, *Flos caryophylli*, coriander herb, *Lignum cupressus funebris*, cassia bark, needle juniper, rhizome of common ginger, fructus citri sinensis, pine leaf, herba ocimi basilic, herba pogostemosis, fructus aurantii, fennel fruits, black pepper, fructus lauri, herba menthae, *Citrus bergamia, Citrus reticulata*, myrrh, herba llimona, rosemary, *Citrus paradisi*, lignum cedrium, herba cymbopogonis citrati, *Salvia officinalis* herb, herba thymni vulgaris, tee tree, perilla leaf, fragrant herb, *Hyssopus officinalis* herb, eucalyptus, lime, fructus limoniae, *Cananga odorata*, cardamom, jasmine, geranium, chamomile, bulgarian rose, rose, frankincense, lavender, sandalwood, neroli oil, herba verbenae, vetiveria zizanoides, *Origanum vulgare* herb, rosewood, *Radix hyperici* monogyni, st. john's malt and euthnnus allecteratus, preferably herba menthae, *Citrus bergamia, Cananga odorata*, geranium, chamomile, lavender, st. john's malt and euthnnus allecteratus that have the effects of calming and relaxing. The forms of the herbs may be, for example, extracts, essential oil, herbal tea and the like, which are not particularly limited. The amino acids are also not particularly limited, which may be, for example, glutamine, glutamic acid, tryptophan, alanine, arginine, aspartic acid, threonine, serine, γ-aminobutyric acid, taurine, thiotaurine and hypotaurine. The vitamins are not particularly limited, which may be, for example, vitamin A, vitamin B1, vitamin B2, vitamin B6, vitamin B12, vitamin C, vitamin D, vitamin E, vitamin K, folic acid, nicotinic acid, lipoic acid, pantothenic acid, biotin, coenzyme Q, prostaglandin and derivatives of these vitamins. In addition, other ingredients include, for example, aloe, royal jelly, melatonin, placenta, propolis, isoflavone, soy lecithin, egg yolk lecithin, egg yolk oil, chondroitin, cocoa mass, collagen, vinegar, chlorella, spirulina, ginkgo leaf, green tea, eucommia tea, oolong tea, mulberry leaf, sweet tea, unsaturated fatty acids, oligosaccharides and other saccharides; *Bifidobacterium*, Japanese koji and other bacteria; Agaricus and other mushrooms; cranberries, dried plums, grapes, olives, Japanese apricots, citrus and other fruits; peanuts, almonds, sesame, chili and other seeds; green chili, red chili, Welsh onions, pumpkins, gourds, carrots, burdock, jute leaf, garlic, basil, *Eutrema yunnanense*, tomatoes, leeks, vegetable leaf, tubers, beans and other vegetables; Undaria pinnatifida and other seaweed; fishes; animals, birds, whales and other meat; cereals and the like. These substances or extracts, dried products, crude purified products, purified products, processed products, brewed products and the like of these substances can be appropriately selected and used as required.

In addition, as an embodiment of this example, a food or drug that contains the composition of this example, is suitable for daily use and is used for individuals with sleep disorders is provided. The food or drug is not particularly limited as long as the composition of the theanine glycoside compound of the present disclosure is contained. Moreover, the "individuals" in this example, with mammals as examples, specifically refer to humans, pigs, cows, dogs, cats, horses and the like, particularly preferably humans.

As the food containing the theanine glycoside compound in this example, various foods can be illustrated as follows.

These foods may include, for example, solid foods, as well as liquid foods such as soft drinks, mineral water, premium drinks and alcoholic beverages. The liquid foods listed herein are not particularly limited, preferably including green tea, oolong tea, black tea, herbal tea and other tea, concentrated fruit juice, concentrated reduced fruit juice, pure fresh fruit juice, compound fruit juice, fruit juice with pulp, beverages with fruit juice, fruit-vegetable compound juice, vegetable juice, mineral water, carbonated beverages, soft drinks, milk, dairy beverages, Japanese wine, beer, wine, cocktail, Soju, Whisky and the like. In addition, the solid foods are also not particularly limited, preferably including sauce products, soy processed products, jelly, lactic acid, cold snacks, sugar, chocolate, chewing gum, crackers, snacks, cookies, bread and the like.

In addition, the drug in this example is not particularly limited as long as the theanine glycoside compound is contained. For example, the form may be any one of a solution, a suspension, a powder, a solid molding product and the like, and the dosage form thereof may include tablets, capsules, powders, granules, beverages and the like. In addition, the composition may also be used in combination with other drugs.

Example 9: Health Care Product Containing a Theanine Glycoside Compound for Promoting Sleep This example provides a health care product for calming the heart, tranquilizing the mind and promoting sleep. A formulation includes, by mass, the following components: 8-12 parts of lily powder, 8-12 parts of a theanine glycoside compound, 8-12 parts of a *Semen ziziphi spinosae* extract, 8-12 parts of a *Ganoderma lucidum* extract, 8-12 parts of mulberry powder, 8-12 parts of lotus seed powder, 3-7 parts of a poria extract, 3-7 parts of a yam extract, 3-7 parts of a ginkgo leaf extract, 3-7 parts of L-tryptophan, 2-5 parts of oryzanol, 0.2-0.8 part of vitamin B1, 0.2-0.8 part of vitamin B6, 0.1-0.4 part of vitamin B12 and 0.005-0.015 part of folic acid; and the final molding dosage form is a powder.

The theanine glycoside compound has a structure shown as follows:

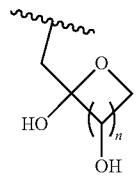

where R is

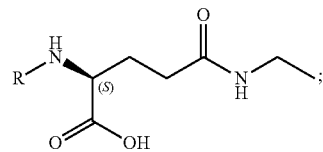

or

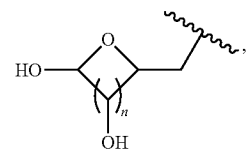

and n is 1-4.

Optionally, the theanine glycoside compound may be any one or more of 1-deoxy-1-L-theanine-D-fructopyranose, 1-deoxy-1-L-theanine-D-galactopyranose and 1-deoxy-1-L-theanine-D-ribopyranose.

Optionally, the formulation preferably includes, by mass, the following components: 10 parts of lily powder, 10 parts of a theanine glycoside compound, 10 parts of a *Semen ziziphi* spinosae extract, 10 parts of a *Ganoderma lucidum* extract, 10 parts of mulberry powder, 10 parts of lotus seed powder, 5 parts of a poria extract, 5 parts of a yam extract, 5 parts of a ginkgo leaf extract, 5 parts of L-tryptophan, 3.5 parts of oryzanol, 0.5 part of vitamin B1, 0.5 part of vitamin B6, 0.25 part of vitamin B12 and 0.01 part of folic acid.

The examples provided above are not intended to limit the scope covered by the present disclosure, and the steps described are also not performed in limited orders. Obvious improvements of the present disclosure made by persons skilled in the art in combination with existing public knowledge also fall within the scope of protection defined in the claims of the present disclosure.

What is claimed is:

1. A product for prolonging half-life of theanine in vivo, wherein the product contains a theanine glycoside compound; and the theanine glycoside compound has a structure shown as follows:

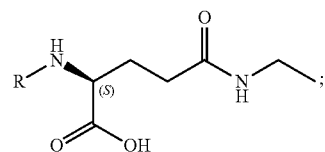

wherein R is

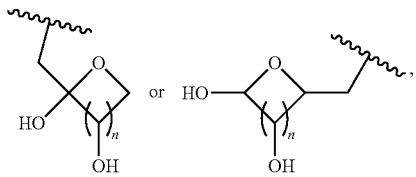

and n is 1-4;
and the theanine glycoside compound is not 1-deoxy-1-L-theanine-D-fructopyranose.

2. A method for prolonging half-life of theanine in vivo, comprising subjecting an amino group in theanine to amination modification by using a monosaccharide to obtain the theanine glycoside compound, wherein the monosaccharide is

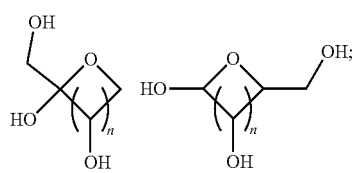

and n is 1-4; and wherein the theanine glycoside compound has a structure shown as follows:

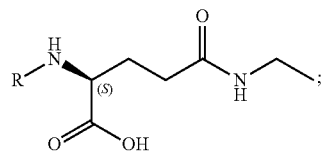

wherein R is

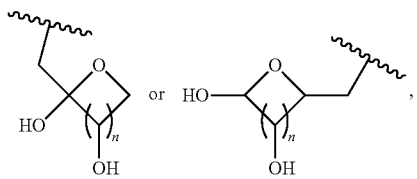

and n is 1-4; and the method further comprises administering a therapeutic dose of the theanine glycoside compound to a subject in need thereof; wherein the theanine glycoside compound is used for prolonging the half-life of theanine in vivo, thereby improving memory and lowering blood pressure.

3. The method according to claim 2, wherein the R is specifically selected from:

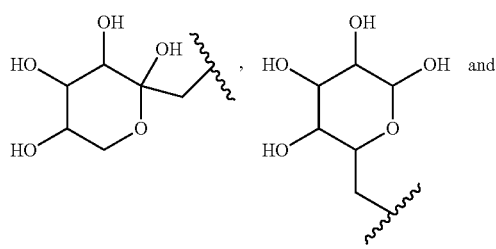

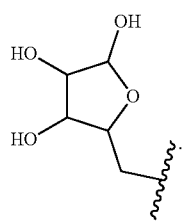

4. A theanine glycoside compound having a structure shown as follows:

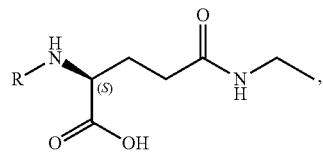

wherein R is selected from

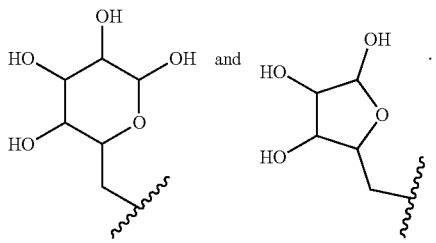 [SMILES: *CC1OC(O)C(O)C(O)C1O ; "and" ; *CC1OC(O)C(O)C1O ; "."]

5. The compound according to claim 4, wherein the theanine glycoside analogue compound is prepared by subjecting an amino group in theanine to amination modification by using a monosaccharide, wherein the monosaccharide is selected from galactose and ribose.

6. The compound according to claim 5, wherein the amination modification comprises the following steps:
(1) subjecting L-theanine as a substrate to amino protection first to obtain an intermediate 1; then subjecting the intermediate 1 to esterification with an alcohol compound to obtain an intermediate 2; and subjecting the intermediate 2 to deamination protection under an action of an acidizing reagent to obtain an intermediate 3;
(2) subjecting the monosaccharide as a substrate to hydroxyl protection and oxidation to obtain an intermediate 4; and
(3) subjecting the intermediate 3 and the intermediate 4 obtained above as a substrate to an amination reduction reaction under an action of a catalyst to obtain an intermediate 5; then subjecting the intermediate 5 to dehydroxylation protection with an acidic reagent to obtain an intermediate 6; and further performing hydrogenation reduction to obtain a target product, namely a theanine glycoside compound.

7. The compound according to claim 6, wherein in step (1), the amino protection comprises reaction processes of: dissolving the L-theanine, an amino protective reagent and an alkaline reagent in a mixed system of tetrahydrofuran and water, and stirring the compounds at room temperature to carry out a reaction to obtain the intermediate 1; the amino protective reagent is Boc$_2$O; a molar ratio of the L-theanine to the amino protective reagent is 1: (1-1.5); the alkaline reagent is Na$_2$CO$_3$ or K$_2$CO$_3$; a molar ratio of the L-theanine to the alkaline reagent is 1: (2-3); a volume ratio of the tetrahydrofuran to the water in the mixed system is 1:1; and a concentration of the L-theanine relative to the mixed system is 20 mg/mL-30 mg/mL.

8. The compound according to claim 6, wherein in step (1), the esterification comprises reaction processes of: in dichloromethane (DCM) as a solvent, subjecting the obtained intermediate 1 and the alcohol compound to dissolution and an esterification reaction under an action of 1-ethyl-3 (3-dimethylpropylamine) carbodiimide (EDCI) and 4-dimethylaminopyridine (DMAP), and stirring the compounds at room temperature to obtain the intermediate 2; the alcohol compound is benzyl alcohol; a molar ratio of the intermediate 1 to the alcohol compound is 1: (1-1.5); a molar ratio of the intermediate 1 to the EDCI is 1:1.5; a molar ratio of the intermediate 1 to the DMAP is 1:0.1; and a concentration of the intermediate 1 relative to the DCM is 20 mg/mL-30 mg/mL.

9. The compound according to claim 6, wherein in step (1), the deamination protection comprises processes of: mixing and stirring the intermediate 2, an HCl/dioxane solution and DCM at room temperature to obtain the intermediate 3.

10. The compound according to claim 6, wherein in step (2), reaction processes comprise: dissolving the monosaccharide in dichloromethane (DCM), and performing stirring in a mixture of dimethyl sulfoxide (DMSO) and oxalyl chloride (COCl)$_2$ as an oxidation system in an environment of N$_2$ at −50° C. to −70° C. for 10 min-40 min to obtain the intermediate 4; a molar ratio of the DMSO to the (COCl)$_2$ in the oxidation system is 2:1; a molar ratio of the monosaccharide to the (COCl)$_2$ is 1:0.5-1:5; and a molar ratio of the intermediate 3 to the intermediate 4 is 1: (0.8-1.5).

11. The compound according to claim 6, wherein in step (3), the catalyst used in the amination reduction is NaBH(COOCH$_3$)$_3$; the amination reduction is performed in DCM as a solvent, and a concentration of the intermediate 3 relative to the DCM is 20 mg/mL-30 mg/ml; the amination reduction reaction is carried out at a temperature of −50° C. to −70° C. for 1 h in a reaction environment of nitrogen; in step (3), the acidic reagent used in the dehydroxylation protection is an HCl solution; in step (3), the hydrogenation reduction comprises dissolving a palladium-carbon catalyst and the intermediate 6 in methanol, introducing hydrogen, and performing stirring at room temperature in an environment of H$_2$ overnight; and a use amount of the palladium-carbon catalyst relative to the intermediate 6 in the process of hydrogenation reduction is 10 wt %.

* * * * *